(12) United States Patent
Yamada et al.

(10) Patent No.: US 8,445,633 B2
(45) Date of Patent: May 21, 2013

(54) PEPTIDE HAVING BINDABILITY WITH ADIPONECTIN, ANALYSIS METHOD UTILIZING SAME PEPTIDE, AND ANALYSIS DEVICE UTILIZING SAME PEPTIDE

(75) Inventors: Mao Yamada, Osaka (JP); Ai Tsutsui, Osaka (JP); Yoshiro Akagi, Osaka (JP); Naoya Ichimura, Kyoto (JP); Atsushi Mizusawa, Kyoto (JP); Takakiyo Tada, Kyoto (JP)

(73) Assignee: Sharp Kabushiki Kaisha, Osaka-Shi, Osaka (JP)

( * ) Notice: Subject to any disclaimer, the term of this patent is extended or adjusted under 35 U.S.C. 154(b) by 24 days.

(21) Appl. No.: 13/094,472

(22) Filed: Apr. 26, 2011

(65) Prior Publication Data

US 2011/0269227 A1 Nov. 3, 2011

(30) Foreign Application Priority Data

Apr. 28, 2010 (JP) ................. 2010-104272

(51) Int. Cl.
- *G01N 33/531* (2006.01)
- *G01N 33/543* (2006.01)
- *A61K 38/04* (2006.01)
- *A61K 38/08* (2006.01)
- *C07K 2/00* (2006.01)
- *C12M 1/40* (2006.01)

(52) U.S. Cl.
USPC ............ 530/300; 530/327; 530/328; 435/7.1; 435/287.1; 436/518

(58) Field of Classification Search
None
See application file for complete search history.

(56) References Cited

U.S. PATENT DOCUMENTS

| | | | |
|---|---|---|---|
| 7,435,808 B2 * | 10/2008 | Wu et al. ..................... | 536/23.5 |
| 2004/0241802 A1 | 12/2004 | Kadowaki et al. | |
| 2005/0048565 A1 | 3/2005 | Tomita et al. | |
| 2005/0266506 A1 | 12/2005 | Tomita et al. | |
| 2007/0037207 A1 | 2/2007 | Tachikawa et al. | |
| 2007/0054314 A1 | 3/2007 | Kadowaki et al. | |
| 2010/0062541 A1 | 3/2010 | Kadowaki et al. | |
| 2012/0027760 A1 | 2/2012 | Kadowaki et al. | |

FOREIGN PATENT DOCUMENTS

| | | |
|---|---|---|
| JP | 2004-333504 A | 11/2004 |
| JP | 2007-111050 | 5/2007 |
| WO | WO-2004/061108 | 7/2004 |
| WO | 2004/086040 A1 | 10/2004 |

OTHER PUBLICATIONS

Lazar et al., (Mol Cell Biol 8(3):1247-52 (1988).*
Rudikoff et al. (PNAS USA, 1982, 79: 1979-1983).*
Coleman et al. (Research in Immunology, 1994; 145(1): 33-36).*
Skolnick et al. (TIBTECH 18:34-39, 2000).*
P.E. Scherer et al., A Novel Serum Protein Similar to C1q, Produced Exclusively in Adipocytes, The Journal of Biological Chemistry, 270(45), pp. 26746-26749 (1995).
C. Weyer et al., "Hypoadiponectinemia in Obesity and Type 2 Diabetes: Close Association with Insulin resistance and Hyperinsulinemia", The Journal of Clinical Endocrinology & Metabolism, 86(5), pp. 1930-1935 (2001).
Wang et al., "Proteomic characterization of human serum proteins associated with the fat-derived hormone adiponectin", Proteomics, 2006, vol. 6, pp. 3862-3870.
Wang et al., "Adiponectin Inhibits Cell Proliferation by Interacting with Several Growth Factors in an Oligomerization-dependent Manner", J. Biol. Chem. 2005, Issue of May, vol. 280, No. 18, pp. 18341-18347.

* cited by examiner

*Primary Examiner* — Peter J Reddig
*Assistant Examiner* — Carmencita M Belei
(74) *Attorney, Agent, or Firm* — Edwards Wildman Palmer LLP; George W. Neuner (57) ABSTRACT

Developed is an adiponectin-recognition material which is inexpensive and excellent in: productivity; stability of quality and a structure; and convenience. The present invention provides a peptide consisting of not more than 50 amino acids and having bindability with adiponectin.

13 Claims, 3 Drawing Sheets

PEPTIDE HAVING BINDABILITY WITH ADIPONECTIN, ANALYSIS METHOD UTILIZING SAME PEPTIDE, AND ANALYSIS DEVICE UTILIZING SAME PEPTIDE

This Nonprovisional application claims priority under 35 U.S.C. §119(a) on Patent Application No. 2010-104272 filed in Japan on Apr. 28, 2010, the entire contents of which are hereby incorporated by reference.

TECHNICAL FIELD

The present invention relates to a technique for analyzing adiponectin. More specifically, the present invention relates to peptides having bindability with adiponectin, and to an analysis method and an analysis device which utilize the peptides.

BACKGROUND ART

Adiponectin (also referred to as ACRP30 or GBP28) is a cytokine which is specifically produced and secreted mainly from adipose tissue, and is a protein consisting of 244 amino acids (see Non-patent Literature 1). It has been demonstrated that adiponectin has an effect of improving an insulin sensitivity, and an effect of accelerating fat burning in a liver and in a muscle. Since adiponectin has such effects, it is expected that normalization of the secretion of adiponectin will make it possible to comprehensively improve symptoms of metabolic syndrome such as high blood pressure, abnormal lipid metabolism, and diabetes (see Non-patent Literature 2).

As for diabetes which is one of diseases caused by metabolic syndrome, the Japanese Ministry of Health, Labor, and Welfare conducted an actual condition survey in 2006. According to the result of the survey: approximately 8.20 million people were strongly suspected of diabetes, and approximately 10.50 million people had an undeniable possibility of diabetes. That is, an estimated 18.70 million people in total were suspected of diabetes. It is said that people suffering from lifestyle-related diseases including diabetes and potential patients will increase, and what is important is to prevent such diseases by improving a lifestyle.

As described above, adiponectin relates to metabolic syndrome. Therefore, it is considered that adiponectin has a possibility of serving as an indicator of lifestyle-related diseases. Accordingly, it is considered that measurement of an in vivo concentration of adiponectin leads to maintenance of good health and to early detection of abnormal metabolism.

A concentration of adiponectin has been heretofore measured by an immunological measurement method in which used as an adiponectin-recognition material is an antibody which is a protein (the antibody is a monoclonal or polyclonal antibody obtained by using adiponectin as an immunogen) (see Patent Literatures 1 and 2). Specifically, Patent Literature 1 discloses a monoclonal antibody which makes it possible to measure a concentration of adiponectin as it is without modifying its natural structure, even though adiponectin is present in the forms of various multimers in blood. In addition, Patent Literature 1 discloses a testing method for Type 2 diabetes in which the monoclonal antibody is utilized. Patent Literature 2 discloses a polyclonal antibody which binds specifically with adiponectin. In addition, Patent Literature 2 discloses a reagent and a method for analyzing adiponectin in which reagent and method latex particles on which the polyclonal antibody is supported.

One of such immunological measurement methods is a sandwich technique utilizing an antibody. In the sandwich technique, specifically, a concentration of adiponectin is measured as below. First, an antibody specific to adiponectin is immobilized in a microplate. Then, a sample containing adiponectin is added thereto in order that adiponectin in the sample may react with the antibody. Adiponectin is thus immobilized in the microplate. Then, adiponectin thus immobilized is further reacted with another antibody which is labeled with an enzyme, a fluorescent compound, or the like, and which is different in epitope from the antibody immobilized in the microplate. Then, the enzyme or the fluorescent compound is detected so as to detect adiponectin.

CITATION LIST

Patent Literature 1
Japanese Patent Application Publication, Tokukai, No. 2004-333504 A (Publication Date: Nov. 25, 2004)
Patent Literature 2
PCT International Application Publication, WO2004/086040 (Date of International Publication: Oct. 7, 2004)
Non-Patent Literature 1
Philipp E. Scherer, et al., J. Biol. Chem., 1995, vol. 270, pp. 26746-26749
Non-Patent Literature 2
Christian Weyer, et al., J. Clin. End. & Metab., 2001, vol. 86, 1930-1935

SUMMARY OF INVENTION

Technical Problem

In the conventional arts, an antibody, which is a protein, is essential for detecting adiponectin. However, production of an antibody takes a long time because an antibody is obtained via animal immunization, hybridoma cell production, and purification following them. This is an obstacle against efficient mass-production of an antibody, and also a cause for high production costs. Furthermore, quality of an antibody varies between production lots. Thus, there is another problem in securing stability of quality.

The effect of an analytical condition (temperature, humidity, pH, enzyme, light, decomposition, or the like) can cause a structural change of a protein, thereby accordingly deactivating the protein. In a case of analysis using an antibody which is a protein so structurally unstable against analytical conditions, the protein would have a change in its bindability with adiponectin, depending on the analytical conditions. That is, analysis utilizing a protein has a problem in that a result of the analysis varies depending on the analytical condition (i.e., reliability of the result is low). Another problem is a possibility that in a case of adiponectin analysis where a protein is immobilized onto a substrate, the immobilization denaturalizes the protein so that the protein is decreased in its bindability with adiponectin. Furthermore, a protein has identical amino acids. That is, the protein has identical functional groups. Therefore, it is also difficult to modify or tag a desired site of the protein.

The present invention was made in view of the problems. An object of the present invention is to provide an adiponectin-recognition material which is inexpensive and excellent in: productivity; stability of quality and a structure; and convenience.

Solution to Problem

From a unique standpoint, the inventors of the present invention found a peptide having bindability with adiponectin, thereby achieving the present invention.

Specifically, a peptide of the present invention consists of not more than 50 amino acids, and has bindability with adiponectin.

The peptide of the present invention has an extremely few amino acids, as compared to a high molecular protein (e.g., antibody). Therefore, (i) the peptide of the present invention can be easily obtained by a chemical synthesis method. (ii) Further, since the peptide does not have a structural change caused by the analytical conditions, the peptide does not decrease in its bindability with adiponectin. (iii) Further, since the peptide does not contain identical amino acids or contains a few identical amino acids, it is possible to easily modify or tag a particular amino acid. Thus, the peptide of the present invention can be used as an adiponectin-recognition material which is inexpensive and excellent in: productivity; stability of quality and a structure; and convenience.

As described above, the peptide of the present invention does not contain identical amino acids or contains a few identical amino acids. Therefore, it is possible to easily immobilize the peptide onto a substrate via a particular site of the peptide. The use of such a substrate makes it possible to remarkably improve convenience of the analysis method and the analysis device, analytical accuracy, and reliability.

Advantageous Effects of Invention

The present invention makes it possible to provide an adiponectin-recognition material which is inexpensive and excellent in: productivity; stability of quality and a structure; and convenience. The use of such an adiponectin-recognition material makes it possible to provide, at low cost, an analysis method and an analysis device which make it possible to obtain a stable analysis result under any analytical condition.

DESCRIPTION OF EMBODIMENTS (1) Peptide of the Present Invention

The present invention provides a peptide which contains not more than 50 amino acids and which is bindable with adiponectin. In the present Description, "peptide" refers to 2 to 50 amino acids which are linked via peptide bond, preferably 7 to 50 amino acids which are linked via peptide bond, or more preferably 7 to 20 amino acids which are linked via peptide bond. In general, an antibody which is one of molecular recognition materials has approximately 10 amino acids in its hypervariable region. This indicates that a peptide consisting of approximately 10 amino acids can recognize a target protein. On the basis of such common general technical knowledge, a person skilled in the art can easily understand that the peptide of the present invention can sufficiently recognize adiponectin, provided that the number of the amino acids falls within any one of the aforementioned ranges. Further, the peptide can be efficiently synthesized by a chemical synthesis method, provided that the number of the amino acids falls within any one of the aforementioned ranges.

In the present Description, "bindability" refers to a binding property brought about by an intermolecular interaction (e.g., electrostatic interaction, $\pi$-$\pi$ interaction, dipolar interaction, hydrophobic interaction, hydrogen bond, coordinate bond, and hydration bond). Therefore, "peptide having bindability with adiponectin" refers to a peptide having a binding property with adiponectin by the intermolecular interaction. The bindability can be assessed by a conventional publicly-known technique such as an enzyme immunoassay and a surface plasmon resonance.

In one embodiment, the peptide of the present invention is a peptide containing the amino-acid sequence represented by any one of SEQ ID NOs: 1 to 15. In another embodiment, the peptide of the present invention is a peptide containing an amino-acid sequence in which one or several amino acids are added or substituted in the amino-acid sequence represented by any one of SEQ ID NOs: 1 to 15.

"Substitution or addition of one or several amino acids" refers to substitution or addition of as many amino acids as a person skilled in the art can easily substitute or add according to a conventional technique (preferably, not more than 10; more preferably, not more than 7; further more preferably, not more than 5; still further more preferably, not more than 3).

The substitution of amino acids is preferably conservative substitution. "Conservative substitution" refers to substitution of another amino acid for a particular amino acid which another amino acid has a chemical property and/or a structure which are similar to those of the particular amino acid. Examples of the chemical property encompass a degree of hydrophobicity (how much it is hydrophobic or hydrophilic) and an electric charge (neutral, acidic, and basic). Examples of the structure encompass: a side chain; and an aromatic ring, an aliphatic hydrocarbon group, and a carboxyl group which are functional groups of a side chain.

Table 1 shows chemical properties and structures of amino acids. In Table 1, the degree of hydrophobicity is expressed such that a larger value indicates a higher hydrophobic property, and a smaller value indicates a higher hydrophilicity. Each of amino acids can be classified by, e.g., whether it has a hydrophobic property or a hydrophilic property.

TABLE 1

| AMINO ACID | SINGLE CHARACTER REPRESENTATION | CHEMICAL PROPERTY | | STRUCTURE SIDE-CHAIN |
| --- | --- | --- | --- | --- |
| | | DEGREE OF HYDROPHOBICITY | ELECTRIC CHARGE | FUNCTIONAL GROUP |
| ISOLEUCINE | I | 4.5 | NEUTRAL | ALIPHATIC HYDROCARBON GROUP |

TABLE 1-continued

| AMINO ACID | SINGLE CHARACTER REPRESENTATION | CHEMICAL PROPERTY DEGREE OF HYDROPHOBICITY | ELECTRIC CHARGE | STRUCTURE SIDE-CHAIN FUNCTIONAL GROUP |
|---|---|---|---|---|
| VALINE | V | 4.2 | NEUTRAL | ALIPHATIC HYDROCARBON GROUP |
| LEUCINE | L | 3.8 | NEUTRAL | ALIPHATIC HYDROCARBON GROUP |
| PHENYLALANINE | F | 2.8 | NEUTRAL | AROMATIC RING |
| CYSTEINE | C | 2.5 | NEUTRAL | SULFUR |
| METHIONINE | M | 1.9 | NEUTRAL | SULFUR |
| ALANINE | A | 1.8 | NEUTRAL | ALIPHATIC HYDROCARBON GROUP |
| GLYCINE | G | −0.4 | NEUTRAL | HYDROGEN |
| THREONINE | T | −0.7 | NEUTRAL | HYDROXYL GROUP |
| SERINE | S | −0.8 | NEUTRAL | HYDROXYL GROUP |
| TRYPTOPHAN | W | −0.9 | NEUTRAL | AROMATIC RING |
| LEUCINE | Y | −1.3 | NEUTRAL | AROMATIC RING |
| PROLINE | P | −1.6 | NEUTRAL | ALIPHATIC HYDROCARBON GROUP |
| ASPARAGINE | N | −3.5 | NEUTRAL | AMIDATED CARBOXYL GROUP |
| GLUTAMINE | Q | −3.5 | NEUTRAL | AMIDATED CARBOXYL GROUP |
| ASPARAGINIC ACID | D | −3.5 | ACIDIC | CARBOXYL GROUP |
| GLUTAMIC ACID | E | −3.5 | ACIDIC | CARBOXYL GROUP |
| HISTIDINE | H | −3.2 | BASIC | AMINO GROUP |
| LYSINE | K | −3.9 | BASIC | AMINO GROUP |
| ARGININE | R | −4.5 | BASIC | AMINO GROUP |

Amino acids having similar chemical properties and/or similar structures can be classified into, e.g., the following five groups (a) to (e), on the basis of hydrophobicities of the amino acids, electric charges thereof, or types of side-chain functional groups thereof.
(a) Group of neutral amino acids having a hydrophilic property: asparagine, glutamine, serine, threonine, and glycine.
(b) Group of acidic amino acids: asparaginic acid and glutamic acid.
(c) Group of basic amino acids: histidine, lysine, and arginine.
(d) Group of neutral amino acids having a hydrophobic property: alanine, isoleucine, leucine, proline, valine, and methionine.
(e) Group of amino acids having an aromatic ring: phenylalanine, tryptophan, and tyrosine.

According to the classification, the conservative substitution can be described as substitution between amino acids in one of the groups. Examples of such substitution encompass substitution between serine and threonine, substitution between lysine and arginine, and substitution between phenylalanine and tryptophan.

Addition of amino acids refers to binding of additional amino acids with an N-terminal and/or a C-terminal of a peptide. The peptide of the present invention may be a plurality of bound peptides each of which is the peptide of the present invention, provided that the plurality of bound peptides have the bindability with adiponectin. The peptide of the present invention and the additional amino acids may be directly bound, or bound via a linker. In a case where the peptide of the present invention is the plurality of bound peptides each of which is the peptide of the present invention, the plurality of bound peptides may be directly bound, or bound via a linker to be described later.

The peptide of the present invention may contain an additional peptide. Examples of the additional peptide encompass epitope-tagging peptides such as His, Myc, and Flag.

The peptide of the present invention are amino acids which are linked via peptide bond. However, the present embodiment is not limited to this. Alternatively, the peptide of the present invention may be a composite peptide having a structure other than structures of peptides. Examples of the structure encompass a sugar chain and an isoprenoid group. Each of the amino acids is preferably one of the 20 types of amino acids shown in Table 1. However the amino acids are not limited to this. A functional group of each of the amino acids may be modified. Each of the amino acids is preferably an L-type amino acid.

The peptide of the present invention is a novel peptide which was independently found by the inventors of the present invention. As described in Examples below, it was proved that the peptide bound with adiponectin. A person skilled in the art cannot easily predict such a function of the peptide of the present invention, on the basis of the amino-acid sequence of the peptide. The peptide of the present invention can be easily produced by any publicly-known technique in the technical field. For example, the peptide may be produced by chemical synthesis or by recombinant expression. Examples of a chemical synthesis method encompass a solid-phase method and a liquid-phase method. In the solid-phase method, it is possible to use, e.g., various commercially-available peptide synthesis apparatuses (e.g., Model MultiPep RS (Intavis AG)).

The peptide of the present invention may contain a linker. This makes it possible to bind the peptides of the present invention via the linker, or bind the peptide of the present invention with another substance (e.g., substrate to be described later) via the linker. In a case where the peptides of the present invention are bound, identical peptides may be bound, or different peptides may be bound.

In the present Description, "linker" refers to a structure which can link two or more substances, without changing properties of the two or more substances. The linker allow the peptide of the present invention to be immobilized to another substance (a substrate, an additional molecule, or the like) via the linker with maintenance of its bindability with adiponectin. The peptide containing the linker may not be actually linked with another substance.

The linker may be bound (e.g., by covalent bond) with, e.g., an amino acid of the peptide of the present invention. More specifically, the linker may be bound with an amino group or a side chain of an amino acid of the N-terminal of the peptide of the present invention. The liner may be bound with a carboxyl group or a side chain of an amino acid of the C-terminal of the peptide of the present invention. Alternatively, the linker may be bound with a side chain of an amino acid other than the amino acids of the N-terminal and the C-terminal. Furthermore, the linker may be bound with an amino group, a carboxyl group, or a side chain of an amino acid added to the N-terminal and/or the C-terminal of the peptide of the present invention.

Preferable examples of the amino acid to be added to the peptide of the present invention encompass lysine, arginine, histidine, and cysteine. It is possible to easily bind the linker with an amino group in a side chain of lysine, arginine or histidine. Similarly, it is possible to easily bind the linker with a thiol group in a side chain of cysteine.

A terminal of the linker preferably has an appropriate functional group so as to bind with the peptide. Examples of such a functional group encompass an amino group, a thiol group, a carboxyl group, and a hydroxyl group. A functional group is employed in accordance with the peptide with which the linker is bound. Preferable functional group is the amino group or the thiol group.

In binding the linker with the peptide of the present invention, it is preferable to protect a functional group of an amino acid other than the amino acid with which the linker is bound. The protection of the functional group may be carried out by a publicly-known method. The protection of the functional group makes it possible to selectively react the linker with a target functional group. This makes it possible to bind the linker with a target side of the peptide.

Examples of the linker encompass a carbon chain, a peptide, and a sugar chain. The carbon chain may be, e.g., a substituted alkyl group or an unsubstituted alkyl group. The carbon chain may contain an oxygen atom, a nitrogen atom, and/or a sulfur atom.

Alternatively, the linker may be a compound (polyethylene glycol (PEG) or the like) having a structure in which oxyalkylene has a functional group at each of both sides.

Further, the linker may be a compound called a cross-linker. Examples of the compound encompass sulfo-SMCC (sulfosuccinimidyl-4-[N-maleimidomethyl]cyclohexane-1-carboxylate). Sulfo-SMCC represented by Chemical Formula 1 has a maleimide group which reacts with a thiol group, and a succinimide group which reacts with an amino group.

Sulfo-SMCC thus has two reacting sites. As represented in Formula 2, this makes it possible to, e.g., bind the maleimide group with the thiol group of the peptide, and bind the succinimide group with the amino group of a compound for tagging (or with an amino group on the substrate).

[Chem. 1]

[Chem. 2]

If the linker is too short, a sufficient space cannot be secured between the peptide and another substance (substrate etc.). As a result, the peptide and another substance tend to interfere with each other. On the other hand, if the linker is too long, the linker tends to be bent. As a result, the peptide can lose its bindability with adiponectin. Therefore, a length of the linker is preferably not less than 0.5 nm but not more than 10 nm (5 Å to 100 Å) although the length is not particularly limited. A type of the linker can be selected in accordance with, e.g., the amino-acid sequence of the peptide or an amino acid which is added to the peptide.

The peptide of the present invention may be tagged. In the present Description, "tag" refers to give that feature to a target substance which is different from other features.

The tag may be addition of a biologically-relevant molecule, or addition of a fluorescent compound. The peptide may be directly tagged, or tagged via the linker. In the present Description, a biologically-relevant molecule and a fluorescent compound are generically also referred to a compound for tagging.

In the present Description, "biologically-relevant molecule" refers to a molecule which may be present in a body of an organism, or to an analog of the molecule. The biologically-relevant molecule may be a naturally-occurring one, an artificially-synthesized one, or a combination thereof. Examples of the biologically-relevant molecule encompass a nucleic acid, a protein (alkaline phosphatase (ALP) and horseradish peroxidase (HRP) which are enzymes, etc.), a peptide, a sugar chain, and a low-molecular compound (a hormone, biotin and avidin, etc.).

Examples of the fluorescent compound encompass fluorescein (FITC), rhodamine and rhodamine derivative, Texas Red, Cy3, and Cy5. However, the fluorescent compound is not limited to them.

At least two types of the peptides of the present invention may be used in combination. For example, two or more types of peptides may be individually immobilized on a substrate to be described later or the like. Alternatively, two or more types of peptides, which are bound directly or via the linker, may be immobilized thereon. By thus employing a plurality of peptides which have respective different sites (epitopes) which bind with adiponectin, the peptides of different types bind with one adiponectin. This makes it possible to increase the bindability with adiponectin. This makes it possible to increase a sensitivity of the analysis method and the analysis device of the present invention.

(2) Substrate of the Present Invention

A substrate of the present invention is a substrate onto which immobilized is the peptide of the present invention. In the present Description, the substrate is not particularly limited, provided that the substrate provides scaffolding for the peptide (i.e., the peptide is accordingly immobilized). Examples of the substrate encompass plastics such as polystyrene and polycarbonate, biological polymers such as cellulose and dextran, metals such as gold (Au), copper (Cu), silver (Ag), platinum (Pt), and titanium (Ti), glass, ceramics, and a resin. These substrates can be used in any form according to use. For example, the substrates may be used in the forms of a basal plate (slide, plate, chip, tube, or the like), a fine particle, a bead, a membrane, etc.

Examples of a method for immobilizing the peptide of the present invention to the substrate encompass a method for immobilizing by adsorption brought about by, e.g., a hydrophilic property or a hydrophobic property, and a method for immobilizing by binding the peptide with the substrate (e.g., by covalent bonding).

The peptide may be directly immobilized to the substrate, or immobilized thereto via the linker or a biologically-relevant molecule. By employing the linker and/or the biologically-relevant molecule, it is possible to bind desired sites of the peptide with the substrate. By thus binding the linker and/or the biologically-relevant molecule with the substrate, it is possible to immobilize the peptide to the substrate, with maintenance of the bindability with adiponectin.

In a case where, e.g., biotin and avidin are employed as biologically-relevant molecules, avidin is first immobilized to the substrate by physical adsorption or by chemical adsorption, and then, a biotin-tagged peptide is added thereto. This makes it possible to immobilize the peptide to the substrate via a bond between avidin and biotin.

In a case where, e.g., used as the linker is a linker having an amino group and a maleimide group, a PEG alkanethiol SAM (Self-Assembled Monolayer) having a carboxyl-modified terminal is first formed on a substrate made from gold. Then, the carboxyl group on the substrate is activated so as to bind with the amino group of the linker. Further, by binding a thiol group of cysteine of the peptide with the maleimide group of the linker, it is possible to immobilize the peptide to the substrate. In a case where a peptide to be employed does not contain cysteine, cysteine is added to the N-terminal or the C-terminal of the peptide by a publicly-known method.

(3) Analysis Method of the Present Invention

The present invention provides a method for analyzing adiponectin. In the analysis method of the present invention, at least one type of peptide of the present invention or the substrate of the present invention is used to analyze adiponectin. More specifically, the analysis method of the present invention includes the step of analyzing a complex of the peptide of the present invention and adiponectin. The step may be a step of analyzing, by a conventional publicly-known method, a signal (absorbance, fluorescence intensity, fluorescence polarization, surface plasmon resonance (SPR), quartz crystal microbalance (QCM), or the like) indicating that adiponectin is bound with the peptide.

The analysis method of the present invention may further include the step of incubating a sample and at least one type of peptide of the present invention. For example, a sample containing adiponectin (or a sample presumed to contain adiponectin) is incubated together with: the peptide dissolved in a solution; a substrate to which the peptide is immobilized; or the like. The step makes it possible to bind adiponectin with the peptide of the present invention.

In this technical field, the term "sample" is used synonymously with specimen or preparation. In the present Description, "sample" refers to "biological sample" or the equivalent thereof. "Biological sample" refers to any preparation obtained from a biological material (e.g., organism, body fluid, cell strain, tissue culture, tissue section, tissue biopsy, etc.) which serves as a source. Examples of the biological sample which is applied to the present invention encompass bodily fluids (e.g., blood, saliva, serum, blood plasma, urine, spinal fluid, and bodily secretion), and the dilution thereof. A preferable biological sample is a sample obtained from a subject (i.e., subject sample). A method for obtaining a tissue biopsy and a bodily fluid from a mammal is well-known in this technical field. Other than the biological sample above, the term "sample" in the present Description also refers to a protein sample, a genomic DNA sample, and/or a total RNA sample which are extracted from the biological sample.

In the present Description, "incubate" refers to putting a plurality of substances in one place so that they sufficiently make contact with each other. As described above, any one of the peptides of the present invention has the bindability with adiponectin. Accordingly, in a case where a sample contains adiponectin, an "the adiponectin-peptide complex" is formed by incubating a sample and the peptide of the present invention. The "incubation" step may be the step of adding the peptide of the present invention to the sample, or the step of mixing the peptide of the present invention with the sample.

In the present Description, "analysis" encompasses quantitative or semiquantitative "measurement" of an amount (e.g., number of moles or concentration) of an objective substance in the sample, and "detection" of the objective substance in the sample. The step of analyzing the complex of the peptide and adiponectin may be the step of detecting the presence of the complex, or the step of measuring an amount of the complex. In the step, it is possible to use various analysis procedures which are publicly-known in this technical field (e.g., a sandwich technique utilizing an antipeptide antibody or an antiadiponectin antibody, a direct technique, and tagging a peptide), or use various analysis measures which are publicly-known in this technical field (i.e., detection of a signal by use of absorbance measurement, fluorescence intensity measurement, fluorescence polarization, surface plasmon resonance (SPR), quarts crystal microbalance (QCM), or the like). The peptides of the present invention are unlikely to have a structural change which is caused by an analytical condition. Therefore, by employing one of the aforementioned analysis procedures and methods, it is possible to obtain a stable result which is not affected by an analytical condition.

In a case where adiponectin is bound with a peptide dissolved in a solution, a fluorescence polarization assay may be used in the analysis method of the present invention. Specifically, for example, once a peptide tagged with a fluorescent compound binds with adiponectin, fluorescence polarization of the fluorescent compound is changed. Therefore, it is possible to detect adiponectin bound with the peptide, on the basis of the presence or absence of the change.

In a case where adiponectin is bound with a peptide immobilized to a substrate or the like, an immunological method such as an enzyme immunoassay, a western blott method, a radioimmunoassay, and an immunoprecipitation method; absorbance measurement; fluorescence intensity measurement; surface plasmon resonance; QCM; or the like may be used in the analysis method of the present invention.

From viewpoints of a detection sensitivity, specificity, and simple operation, the enzyme immunoassay is preferably used in the analysis method of the present invention. The enzyme immunoassay is not particularly limited but may be the direct technique or the sandwich method.

In a case where the sandwich technique is used in the analysis method of the present invention, a first peptide is immobilized in a well of a plate first. Then, blocking is performed in the well by use of a polymer or a protein such as bovine serum albumin (BSA) and casein. Then, a sample is incubated in the well. As a result, adiponectin in the sample binds with the first peptide.

After the well is washed, a second peptide tagged with an enzyme is incubated in the well. As a result, the second peptide binds with adiponectin. The well is washed again. Then, a substrate solution for the enzyme is incubated in the well. Accordingly, the substrate solution reacts with the enzyme so that a reaction product is generated. It is possible to detect adiponectin bound with the peptide, on the basis of the presence or absence of such a reaction product. A person skilled in the art can select such a method in accordance with a type of an employed substrate.

In a case where, e.g., employed is a substrate which generates fluorescence by the reaction, it is possible to detect adiponectin by directly observing the fluorescence emitted from the substrate. Further, in a case where employed is a substrate which generates a pigment by the reaction, it is possible to detect adiponectin by measuring an absorbance of the pigment. In a case where employed is a substrate whose electrochemical activity is changed by the reaction, it is possible to detect adiponectin by an electrochemical measure utilizing an electrode.

By performing the sandwich technique in accordance with above procedure, it is possible to determine the presence or absence of adiponectin in the sample. Measurement of a concentration of adiponectin in the sample may be performed as below, for example. First, a signal (fluorescence intensities, absorbances, electrochemical signals, or the like) is measured in advance in the same fashion by use of standard adiponectin solutions of known concentrations, in order to obtain a standard curve which indicates the relationship between the signal and the concentration of adiponectin. A level of the signal obtained from the sample is converted into a concentration of adiponectin, on the basis of the standard curve. In this way, the concentration of adiponectin in the sample is measured.

The above deals with the second peptide tagged with an enzyme. Instead, it is possible to employ a peptide tagged with a fluorescent compound. In a case where employed is the second peptide tagged with a fluorescent compound, it is possible to detect or measure adiponectin by observing fluorescence emitted from the second peptide.

By employing surface plasmon resonance or QCM as the analysis method of the present invention, it is possible not only to detect adiponectin bound with the peptide immobilized to the substrate but also directly measure an amount thereof.

(4) Analysis Device of the Present Invention

The present invention provides a device for analyzing adiponectin. Specifically, the present invention provides an analysis device for performing the analysis method above. In the present Description, "analysis device" refers to a device with an arrangement required for a series of operations for capturing adiponectin into the device, converting, into a signal, information indicating that adiponectin has been captured, and detecting the signal.

In order to analyze adiponectin in the sample, a device of the present invention for analyzing adiponectin, includes: a sample receiving section for receiving a sample; and a capturing section for capturing adiponectin, the capturing section being provided inside the sample receiving section, a peptide of the present invention being immobilized onto the capturing section or a substrate of the present invention being provided in the capturing section.

Figure 1:
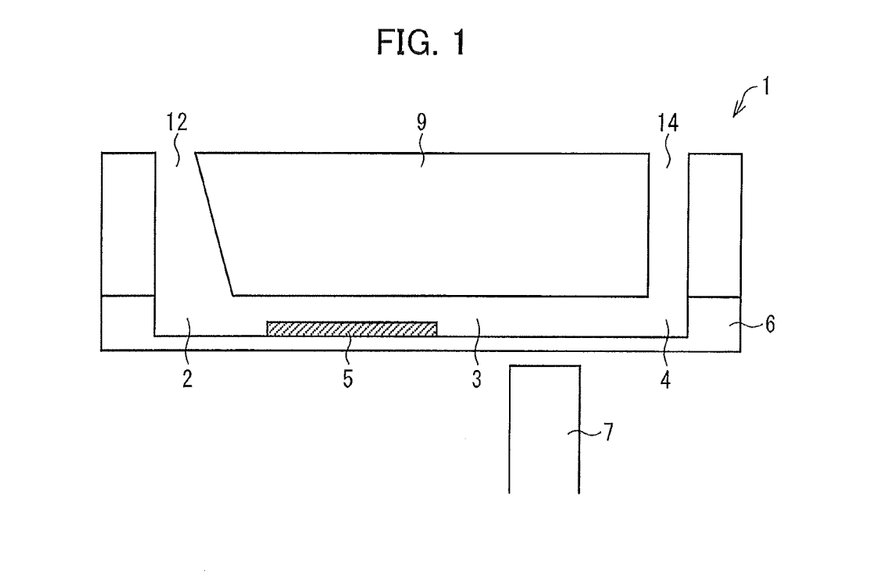
FIG. 1 is a schematic cross-sectional view illustrating one embodiment of an analysis device of the present invention.
Figure 2:
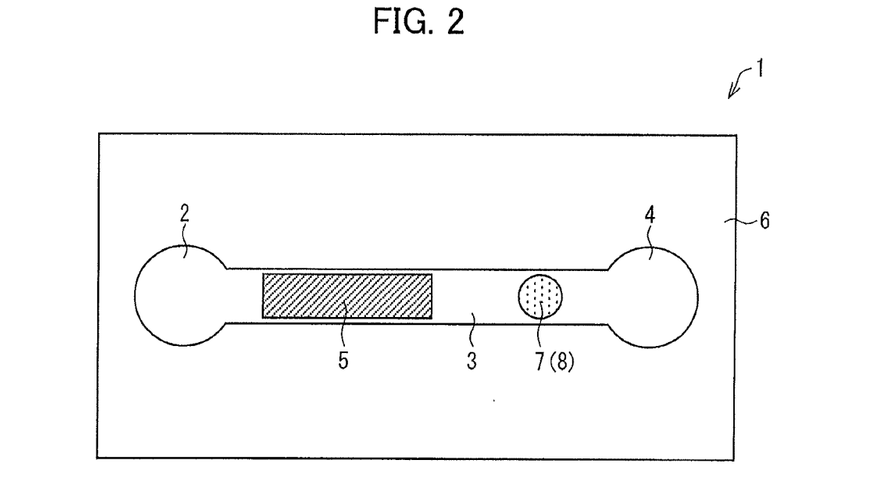
FIG. 2 is a schematic top view illustrating the one embodiment of the analysis device of the present invention.

The following describes the analysis device of the present invention, with reference to FIGS. 1 and 2. FIG. 1 is a side cross-sectional view of an analysis device 1 of the present invention. FIG. 2 is a plan view of the analysis device 1 of the present invention. The following describes the present invention by exemplifying an analysis device of a microchannel type which allows a sample to pass therethrough as fluid. However, a flow channel for passing a sample therethrough is not limited to the microchannel but may be, e.g., a microcapillary. In addition, the present Description allows a person skilled in the art to easily understand that the present invention also encompasses an arrangement which does not allow a sample to pass through the analysis device as fluid (e.g., the well described in "(3) Analysis method of the present invention"). Such an analysis device of the microchannel type takes, e.g., the form of a chip.

The analysis device 1 of the present invention includes a basal plate 6 and a lid 9 which is stacked on the basal plate 6. Provided on a surface of the basal plate 6 is a microchannel 3 having a concave surface. In the present Description, "micro" refers to a size of the order of micrometers, specifically, to a size which can be achieved by a microfabrication technique for semiconductors.

Provided on the surface of the basal plate 6 are a supplying section 2 for receiving a fluid or a sample to be supplied to the microchannel 3, and a discharging section 4 for discharging the fluid from the microchannel 3. The supplying section 2 and the discharging section 4 are connected with both ends of the microchannel 3, respectively. That is, the microchannel 3 connects the supplying section 2 and the discharging section 4 with each other on the surface of the basal plate 6.

The supplying section 2 is an entrance for supplying, to the microchannel 3, a sample to be analyzed and a fluid to be used in the analysis. The supplying section 2 may also have a function of reserving, in advance, the sample to be analyzed or the fluid to be used in the analysis. The discharging section 4 is an outlet for discharging, from the microchannel 3, the analyzed sample and the fluid used in the analysis. The discharging section 4 may also have a function of reserving the discharged sample and fluid.

By stacking the lid 9 on the basal plate 6, the microchannel 3 is separated from the outside of the basal plate 6. However, through-holes (inlet hole 12, outlet hole 14) which penetrate the lid 9 connect the supplying section 2 and the discharging section 4 with the outside of the basal plate 6, respectively. This makes it possible to supply a fluid from the outside of the basal plate 6 to the microchannel 3 via the inlet hole 12, and discharge the fluid from the microchannel 3 to the outside of the basal plate 6 via the outlet hole 14.

According to the present embodiment, the microchannel, the supplying section, and the discharging section are provided in the basal plate. However, they may be provided to the lid. In this case, through-holes (inlet hole, outlet hole) which penetrate the basal plate connect the supplying section and the discharging section with the outside of the basal plate, respectively.

Further, the microchannel 3 includes an immobilizing section 5 for immobilizing the peptide of the present invention. The immobilizing section 5 is for capturing adiponectin in the fluid flowing through the microchannel 3. Provided between the immobilizing section 5 and the discharging section 4 is an analysis section 8 for analyzing adiponectin captured by the immobilizing section 5. An analysis means 7 for detecting adiponectin is provided toward the analysis section 8.

Although this is not illustrated, the analysis device 1 may be arranged such that a drive measure for promoting movement of the fluid in the microchannel 3 from the supplying section 2 to the discharging section 4 is connected with at least any one of the supplying section 2 and the discharging section 4. Examples of such a drive measure encompass an extrusion pump and a suction pump. In a case where the extrusion pump is used to feed the fluid into the microchannel 3, the extrusion pump is joined to the supplying section 2. In a case where the suction pump is used to draw the fluid from the microchannel 3, the suction pump is joined to the discharging section 4.

Examples of a material for the basal plate 6 and the lid 9 encompass plastic materials, glass, quartz, photocurable resins, and thermosetting resins. Top-view shapes of the inlet hole 12 and the outlet hole 14 are not particularly limited but may be a circle, an ellipse, a rectangle, or the like. Top-view shapes of the supplying section 2 and the discharging section 4 which are provided on the basal plate 6 are not particularly limited but may be a circle, an ellipse, a rectangle, or the like. Those shapes of bottom surfaces of the supplying section 2 and the discharging section 4 which are perpendicular to flow directions of the fluid therein may be a linear shape or a half circle.

The microchannel 3 may have a prismatic shape or a cylindrical shape along the flow direction of the fluid. That is, a cross-sectional shape of the microchannel 3 which is perpendicular to the flow direction of the fluid may be a rectangle, a trapezoid, or a circle (half circle). The microchannel 3 is not always required to have a linear shape. Alternatively, the microchannel 3 may have a meandering shape, a spiral shape, or a helical shape.

A width of the microchannel 3 is preferably, e.g., not less than 1 μm but not more than 5000 μm, and a depth thereof is preferably, e.g., not less than 1 μm but not more than 5000 μm. However, the width and depth are not limited to these ranges. Diameters of the supplying section 2 and the discharging section 4 are preferably, e.g., not less than 1 μm but not more than 10000 μm, and depths thereof are preferably, e.g., not less than 1 μm but not more than 5000 μm. However, the diameters and depths are not limited to these ranges. Diameters of the inlet hole 12 and the outlet hole 14 are preferably, e.g., not less than 1 μm but not more than 10000 μm, and depths thereof are preferably, e.g., not less than 1 μm but not more than 10000 μm. However, the diameters and depths are not limited to these ranges.

The peptide can be directly immobilized to the immobilizing section 5 on the basal plate 6 by a method similar to the method for immobilizing the peptide to the substrate. Instead of directly immobilizing the peptide to the basal plate, for example, a substrate onto which the peptide is immobilized may be placed in the immobilizing section 5. Such a substrate may be, e.g., a chip or a bead. In a case where a bead is employed as the substrate, the bead is introduced into the microchannel 3 so as to form the immobilizing section 5. Specifically, a damming section is provided in the microchannel 3 so that the bead held back by the damming section is used as the immobilizing section 5.

The analysis means 7 for analyzing adiponectin may be, e.g., a thermal lens microscope, a surface plasmon resonance measurement device, or a crystal oscillator.

In a case where a light detection is employed in the analysis of adiponectin, the analysis means 7 may include a light source and an analyzer. The light source is preferably selected from the group consisting of a laser, an LED, and a lamp. The analyzer is preferably a photomultiplier tube or a multi-pixel light detector.

In a case where electrochemical detection is employed in the analysis of adiponectin, the analysis means 7 may include an electrode. The electrode is made up of at least two electrodes: a reference electrode and a working electrode. The electrode is preferably made up of three electrodes: the reference electrode, the working electrode, and a counter electrode. The reference electrode, the working electrode, and the counter electrode can be formed in the analysis section 8 by a microfabrication technique based on a conventional photolithographic technique. Examples of a material for the electrode encompass metals such as gold (Au), copper (Cu), silver (Ag), platinum (Pt), and titanium (Ti), and conductive plastics.

According to the description above, the immobilizing section 5 and the analysis section 8 are provided in different positions in the microchannel 3. However, the immobilizing section 5 may also serve as the analysis section 8. In other words, the analysis means 7 may be directed at the immobilizing section 5.

The following describes one example of a method for analyzing adiponectin by use of the analysis device of the present embodiment. The drive measure for promoting movement of the fluid in the microchannel 3 may employ any one of the following methods: a method utilizing the extrusion pump joined to the supplying section 2; a method utilizing the suction pump joined to the discharging section 3; and a method utilizing a capillary force and/or a water-absorbing substance.

1. Blocking

A nonspecific adsorption inhibitor is introduced from the supplying section 2 so that the microchannel 3 is filled therewith, in order to prevent that substance other than adiponectin which is contained in the sample (i.e., substance which is supposed not to be detected) from being adsorbed in a nonspecific fashion to the microchannel 3, the immobilizing section 5, and the analysis section 8. Then, the nonspecific adsorption inhibitor is discharged from the discharging section 3. Then, a wash solution is introduced from the supplying section 2. The wash solution is passed through the microchannel 3, and then discharged from the discharging section 4. Thus, unnecessary nonspecific adsorption inhibitor remaining in the microchannel 3 is removed. Examples of a preferable nonspecific adsorption inhibitor encompass bovine serum albumin (BSA), casein, and polymers.

2. Introduction of the Sample

The sample is introduced from the supplying section 2 into the microchannel 3. The sample is passed through the microchannel 3 so as to reach the immobilizing section 5. While the sample is passed through the immobilizing section 5, adiponectin in the sample binds with the first peptide in the immobilizing section 5. Thus, adiponectin is captured at the immobilizing section 5. Then, the wash solution is introduced from the supplying section 2. The wash solution is passed through the microchannel 3, and then, discharged from the discharging section 4. Thus, an unnecessary sample remaining in the microchannel 3 is removed.

The sample may be moved in a continuous manner or in a discontinuous manner in the microchannel 3 from the supplying section 2 to the discharging section 3. In a case where the sample is moved in a discontinuous manner, the sample may be, e.g., incubated for a predetermined period in an area of the immobilizing section 5. By thus incubating the sample, it is possible to optimize a time of reaction between the peptide and adiponectin in the sample.

3. Tagging of Adiponectin Captured by Immobilizing Section

The second peptide which is tagged is introduced from the supplying section 2 to the microchannel 3 so as to reach the immobilizing section 5. While the second peptide is passed through the immobilizing section 5, the second peptide binds with adiponectin captured by the immobilizing section 5. As a result of this operation, adiponectin is tagged which is captured by the immobilizing section 5.

4. Analysis of Adiponectin

By detecting the tag of adiponectin by use of the analysis means 7, it becomes possible to analyze adiponectin by the analysis section 8. Examples of the compound for tagging encompass fluorescent compounds and enzymes.

4-1. Analysis of Adiponectin by Use of Fluorescent Compound

In case where the compound for tagging is a fluorescent compound in "3. Tagging of adiponectin captured by immobilizing section," adiponectin can be analyzed by directly observing fluorescence from the analysis section 8.

4-2. Analysis of Adiponectin by Use of Enzyme

In case where the compound for tagging is an enzyme in "3. Tagging of adiponectin captured by immobilizing section," the peptide of the present invention containing the enzyme is first caused to bind with adiponectin, and then, a substrate solution for the enzyme is introduced from the supplying section 2 into the microchannel 3. While the substrate solution is passed through the immobilizing section 5, the enzyme of that peptide of the present invention which is bound with adiponectin reacts with the substrate solution. A signal which is obtained as a result of the reaction may be detected by a publicly-known method. Thus, adiponectin can be analyzed. A person skilled in the art can select such a method in accordance with a type of an employed substrate.

In a case where, e.g., employed is a substrate which generates fluorescence by the reaction, it is possible to detect adiponectin by directly observing the fluorescence emitted from the substrate by use of the analysis section 8. In a case where employed is a substrate whose absorbance is changed by the reaction, it is possible to analyze adiponectin by measuring an absorbance in the analysis section 8. In a case where employed is a substrate whose electrochemical activity is changed by the reaction, it is possible to detect adiponectin by an electrochemical measure utilizing an electrode.

It is possible to analyze adiponectin without use of any compound for tagging. In this case, the analysis means 7 may be a thermal lens microscope, a surface plasmon resonance measurement device, a crystal oscillator, or the like.

(5) Gene of the Present Invention

A gene of the present invention is a gene which encodes the peptide of the present invention. In the present Description, the term "gene" is used synonymously with "polynucleotide," "oligonucleotide," "nucleic acid," or "nucleic acid molecule," and refers to a nucleotide polymer. In the present Description, "oligonucleotide" refers to one which consists of 2 to several dozen nucleotides, more specifically, an oligonucleotide which consists of 2 to 50 nucleotides. "Polynucleotide" refers to one which consists of several dozen or more nucleotides, more specifically, a polynucleotide which consists of more than 50 nucleotides.

In the present Description, a nucleotide may be a deoxyribonucleotide or a ribonucleotide.

In the present Description, the term "nucleotide sequence" is used synonymously with "nucleic acid sequence" and "base sequence." A nucleotide sequence is represented as a sequence of a deoxyribonucleotide (abbreviated as A, G, C, and T) or a ribonucleotide.

The gene of the present invention can take the form of an RNA (e.g., mRNA, siRNA, RNAi, and microRNA) or a DNA (e.g., cDNA and genomic DNA). The DNA and the RNA each may be single-stranded or double-stranded one. The single-stranded DNA or RNA may be a coding strand (also known as a sense strand) or a noncoding strand (also known as an antisense strand).

A person skilled in the art can easily obtain a desired gene, on the basis of the amino-acid sequence of the peptide of the present invention. The gene of the present invention can be fused, at its 5' or 3' terminal, with a gene which encodes the tag (i.e., tag sequence or marker sequence).

The gene of the present invention may be a gene which is hybridizable with a gene complementary to the gene of present invention under stringent conditions, and which encodes the peptide having the bindability with adiponectin.

Hybridization may be performed by a publicly-known method such as a method described in "Molecular Cloning: A Laboratory Manual, $3^{rd}$ Ed., Edited by J. Sambrook and D. W. Russell, Cold Spring Harbor Laboratory, NY (2001)," which is incorporated herein by reference in its entirety. Usually, a higher temperature and a lower salt concentration lead to a higher stringency (i.e., it becomes more difficult to perform the hybridization). This makes it possible to obtain a more homologous gene. An appropriate hybridization temperature varies depending on a nucleotide sequence and the length thereof. A person skilled in the art can determine the temperature appropriately.

In the present Description, the term "stringent condition for hybridization" refers to performing overnight incubation and subsequent wash of a filter. The overnight incubation is performed at 42° C. by use of a hybridization solution (containing 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured sheared salmon sperm DNA). The washing of the filter is then performed in 0.1×SSC at approximately 65° C. However, the washing conditions under high stringency vary depending on a polynucleotide employed in the hybridization. In a case where, e.g., employed is a mammal-derived DNA, the washing is preferably performed in 0.5×SSC containing 0.1% SDS at 65° C. (preferably, two times each of which takes 15 minutes). In a case where employed is an E. coli-derived DNA, the washing is preferably performed in 0.1×SSC containing 0.1% SDS at 68° C. (preferably, two times each of which takes 15 minutes). In a case where employed is an RNA, the washing is preferably performed in 0.1×SSC containing 0.1% SDS at 68° C. (preferably, two times each of which takes 15 minutes). In a case where employed is an oligonucleotide, the washing is preferably performed in 0.1×SSC containing 0.1% SDS at a temperature for the hybridization (preferably, two times each of which takes 15 minutes).

(6) Recombinant Vector of the Present Invention

A recombinant vector of the present invention contains the gene of the present invention. For example, the recombinant vector is a recombinant expression vector to which inserted is the gene which encodes the peptide of the present invention. As described later, by introducing such a recombinant expression vector into a host, it is possible to generate, in the host, the peptide of the present invention.

A concrete type of the recombinant expression vector is not particularly limited. Therefore, it is possible to appropriately select a vector which can express the gene in the host. That is, a promoter sequence which leads to expression of the gene of the present invention is selected according to a type of the host, and the selected promoter sequence and the gene of the present invention are integrated into a plasmid (pBR322, pBR325, pUC18, pUC118, or the like), a phage, a cosmid, a virus (retrovirus, vaccinia virus, baculovirus, or the likes), or the like so that the recombinant expression vector is selected therefrom.

The promoter may be an appropriate one which is suitable for the host to be used in the gene expression. In a case where the host is *E. coli*, examples of the promoter encompass a trp promoter, a lac promoter, a recA promoter, a λPL promoter, and an lpp promoters. In a case where the host is an animal cell, examples of the promoter encompass an SRα promoter, an SV40 promoter, an LTR promoter, a CMV promoter, and an HSV-TK promoter.

It is possible to add as necessary, to the recombinant vector of the present invention, an enhancer, a splicing signal, a poly-A additional signal, a selective marker, an SV40 replication origin, or the like. Further, the recombinant vector of the present invention may contain a gene which encodes an additional protein (e.g., glutathione S-transferase, protein A, and GFP (Green Fluorescent Protein)) so that a fusion protein made up of the peptide of the present invention and the additional protein is expressed in the host.

The recombinant vector of the present invention preferably contains at least one selective marker. Examples of such a selective marker encompass: a dihydrofolic acid reductase gene or a neomycin-resistant gene for eukaryote cell culture; and a tetracycline-resistant gene and an ampicillin-resistant gene for the culture of *E. coli* and other bacteria. By use of the selective marker, it is possible to check whether or not the recombinant vector of the present invention has been introduced into the host, and whether or not the gene of the present invention is expressed in a host cell.

The host is not particularly limited. Examples of the host encompass cells, microorganisms, a plant, and animals (except humans). Examples of the cell encompass insect cells (sf9 cells) and animal cells (monkey cells COS-7, Vero, Chinese hamster cells CHO, mouse L cells, mouse AtT-20 cells, mouse myeloma cells, rat GH3 cells, and human FL cells). Examples of the microorganisms encompass *E. coli*, and yeasts (budding yeast (*Saccharomyces cerevisiae*), fission yeast (*Schizosaccharomyces pombe*), etc.).

A method of the present invention for introducing the recombinant vector into a host cell, i.e., a transformation method is not particularly limited. Therefore, it is possible to suitably employ a conventional well-known method such as a calcium phosphate method, a liposome method, a DEAE dextran method, a gene gun, a PEG method, and an electroportion method.

(7) Transformant

A transformant of the present invention contains the recombinant vector of the present invention. Organisms to be transformed are not particularly limited but may be the aforementioned hosts. That is, in the present Description, "transformant" encompasses not only cells but also individual organisms.

A method for producing (or manufacturing) the transformant is not particularly limited. Examples of the method encompass the transformation method in which the recombinant vector of the present invention is introduced into the host by use of a publicly-known transformation method as described above.

A method for selectively harvesting the transformant can be performed by a conventional publicly-known method by use of, e.g., the selective marker contained in the recombinant vector of the present invention.

Whether or not the recombinant vector of the present invention has been introduced into the host can be determined by PCR, a Southern hybridization method, a Northern hybridization method, or the like. For example, PCR may be performed with a DNA obtained from the host into which the recombinant vector of the present invention has been introduced, and with a primer designed to be specific to the gene or the vector of the present invention. A product amplified by PCR is subjected to agarose gel electrophoresis, polyacrylamide gel electrophoresis, capillary electrophoresis, or the like. Then, the resulting product is detected by use of ethidium bromide, an SYBR Green solution, or the like. Thus, it is possible to confirm that the recombinant vector of the present invention has been introduced into the host (i.e., confirm that the host has been transformed). Alternatively, PCR can be performed by use of a primer which is tagged in advance with a fluorescent pigment or the like, so that the amplified product becomes detectable.

The transformant of the present invention thus obtained can be used in a publicly-known method so that the peptide of the present invention is mass-produced. In a case where, e.g., the host is a cell, culture of the cell containing the recombinant vector of the present invention leads to the expression of the gene of the present invention. The peptide of the present invention is thus produced. The peptide of the present invention thus produced in the cell can be purified by a publicly-known method.

The present invention also encompass the following modes.

The peptide of the present invention may be arranged such that the peptide is a peptide including the amino-acid sequence represented by any one of SEQ ID NOs: 1 to 15; or the peptide is a peptide including an amino-acid sequence in which one or several amino acids are added or substituted in the amino-acid sequence represented by any one of SEQ ID NOs: 1 to 15, and having the bindability with adiponectin.

With regard to the peptide of the present invention, the substitution of amino acids is preferably conservative substitution. The substitution is preferably substitution between two amino acids selected from any one of the groups: (a) asparagine, glutamine, serine, threonine, and glycine; (b) asparaginic acid and glutamic acid; (c) histidine, lysine, and arginine; (d) alanine, isoleucine, leucine, proline, valine, and methionine; and (e) phenylalanine, tryptophan, and tyrosine.

The peptide of the present invention preferably consists of not more than 20 amino acids, and may consists of the amino-acid sequence represented by any one of SEQ ID NOs: 1 to 15, 18, and 19.

The peptide of the present invention may contain a linker.

Further, the peptide of the present invention may be tagged. In the present Description, "tag" refers to give that feature to a target substance which is different from other features, and "tag" may be adding a molecule which can reside in an organism or adding the analog thereof (so-called biologically-relevant molecule), or adding a fluorescent compound. Examples of the biologically-relevant molecule encompass enzymes (alkaline phosphatase (ALP) and horseradish peroxidase (HRP), etc.), biotin, avidin, streptavidin, etc. However, the biologically-relevant molecule is not limited to them. The peptide of the present invention may be tagged via the liner, or may be tagged without the linker. In the present Description, a biologically-relevant molecule and a fluorescent compound are generically also referred to as compound for tagging.

In order to analyze adiponectin, a method of the present invention for analyzing adiponectin by using at least one type of peptide of the present invention. The method preferably further includes analyzing a complex of at least one type of peptide of the present invention, and adiponectin. More preferably, in order to analyze adiponectin in a sample, the method further includes incubating at least one type of peptide of the present invention, and the sample.

The peptide of the present invention may be immobilized onto the substrate. That is, the substrate of the present invention is a substrate onto which at least one type of peptide of the present invention is immobilized. The arrangement makes it possible to easily analyze adiponectin by employing various publicly-known analysis procedures (e.g., microchip technology) which are performed on a substrate.

In order to analyze adiponectin, a method of the present invention for analyzing adiponectin by using the substrate of the present invention. Preferably, the method further includes analyzing a complex of the peptide on the substrate of the present invention and adiponectin. In order to analyze adiponectin in a sample, more preferably, the method further includes incubating the substrate of the present invention and the sample. The arrangement makes it possible to directly or indirectly analyze adiponectin bound with the peptide of the present invention immobilized onto the substrate. Examples of the direct analysis method encompass SPR and QCM. Examples of the indirect analysis method encompass the sandwich technique utilizing a secondary biological recognition material (e.g., antibody).

Thus, used in the analysis method of the present invention may be a peptide immobilized onto the substrate, or a peptide which is not immobilized. In a case where the peptide may be immobilized onto the substrate, adiponectin immobilized onto the substrate via the peptide is detected by, e.g., SPR or QCM. In a case where the peptide is not immobilized onto the substrate, a fluorescently-tagged peptide may be used to form a complex with adiponectin in a solution, in order that generated fluorescent polarization is then measured.

In order to analyze adiponectin, a device of the present invention for analyzing adiponectin includes at least one type of peptide of the present invention. The peptides of the present invention are unlikely to have a structural change which is caused by an analytical condition. Therefore, the analysis device makes it possible to obtain a stable analysis result which is not affected by an analytical condition.

In order to analyze adiponectin, the device of the present invention for analyzing adiponectin includes the substrate of the present invention. The arrangement makes it possible to provide, to the analysis device, a measure for directly or indirectly analyzing adiponectin.

In order to analyze adiponectin, a device of the present invention for analyzing adiponectin, includes: a sample receiving section for receiving a sample; and a capturing section for capturing adiponectin, the capturing section being provided inside the sample receiving section, the peptide of the present invention being immobilized onto the capturing section or the substrate of the present invention being provided in the capturing section. The analysis section may be defined in advance as a predetermined position inside the sample receiving section. Alternatively, the analysis section may be provided in accordance with a type and a setting of the analysis measure. That is, according to the latter provision, the analysis section is defined as an area where the analysis measure can perform analysis.

The present invention may be arranged such that the sample receiving section has a flow channel. In this case, the analysis section may be provided downstream of the capturing section. In a case where the sample receiving section has a flow channel, the sample receiving section is made up of the flow channel and an supplying section for supplying a fluid into the flow channel. In this case, the sample receiving section may include a discharging section for discharging the fluid from the flow channel although it is not essential. In the present Description, the terms "upstream" and "downstream" express concepts on the basis of a flowing direction of the fluid in the flow channel. Unless otherwise noted, "upstream" indicates a supplying section side of the fluid in the flow channel, and "downstream" indicates a discharging section side of the fluid. The analysis device of the present invention may be that analysis device having a microchannel which is formed on a substrate.

A gene of the present invention encodes the peptide of the present invention. A recombinant vector of the present invention contains the gene of the present invention. A transformant of the present invention contains the recombinant vector of the present invention.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

EXAMPLES

The following describes the present invention more concretely by showing examples. It should be noted that the scope of the present invention is not limited to the examples.

Example 1

Synthesis of Peptide on Cellulose Membrane (Spot Synthesis)

In order to identify an amino-acid sequence having bindability with adiponectin, a peptide was synthesized on a cellulose membrane by use of a peptide synthesis device (Model MultiPep RS (Intavis AG)) utilizing a Fmoc-based peptide spot synthesis.

Immobilized on the cellulose membrane was polyethylene glycol having a terminal modified with an amino group. An Fmoc amino acid was bound with the amino group by using DIC (diisopropylcarbodiimide)/HOBt (hydroxybenzotriazole). After that, Fmoc was removed. Then, by using DIC/HOBt, another Fmoc amino acid was bound with the amino group of the amino acid which was revealed by the removal of Fmoc.

The cycle of the removal of Fmoc and the subsequent binding was repeated to synthesis a peptide. Then, N-terminals and side chains of all the peptides were deprotected. Thereby, peptides consisting of amino-acid sequences represented by SEQ. ID NOs: 1 to 15 were obtained.

Measurement of Bond Between Peptide and Adiponectin by Enzyme Immunoassay

The sandwich technique which is one of enzyme immunoassays was performed to measure the bond between each of the peptides thus synthesized and adiponectin.

First, a cellulose membrane was soaked in ethanol. Then, the cellulose membrane was continuously washed with phosphate buffered saline (PBS) (pH 7.4) so that ethanol contained in the cellulose membrane was replaced with PBS. In order that nonspecific binding is inhibited, the cellulose membrane was incubated overnight in a blocking solution (PBS containing 1% milk powder).

Then, the cellulose membrane was incubated for 1 hour in a blocking solution (PBS containing 1% milk powder) which contains 0.25 μg/mL human adiponectin (R&D Systems).

Then, the cellulose membrane was washed with PBST (PBS containing 0.1% (v/v) Tween 20). Then, the cellulose membrane was incubated for 1 hour in a blocking solution containing 0.25 g/mL anti-human adiponectin antibody (R&D Systems) which is tagged with HRP, and then washed with PBST five times.

After that, 100 μM fluorescent substrate (Amplex Red (Invitrogen)) containing 1 mM hydrogen peroxide was added to the cellulose membrane, and then they react with each other for 10 minutes. A fluorescent intensity in a synthesis spot was measured in such a manner that an absorption wavelength of 595 nm of fluorescence from the fluorescent substrate was measured by a fluorescence imager (GE Healthcare) by exciting, with light of 540 nm, the fluorescent substrate in the synthesis spot. A bond strength of the peptide was worked out from the fluorescent intensity in the synthesis spot.

Comparative Example 1

A peptide consist of the amino-acid sequence represented by SEQ ID NO. 16 was synthesized as in Example 1. Then, the bond between the synthesized peptide and adiponectin was measured as in Example 1.

Table 2 shows, in abbreviation, amino-acid sequences of the peptides in Example 1 and Comparative Example 1.

TABLE 2

| SEQ ID NO | AMINO-ACID SEQUENCE |
|---|---|
| 1 | VRVLTLPL |
| 2 | LTLPLQAHHAME |
| 3 | LLHGHRPPMP |
| 4 | FRIHTETG |
| 5 | ILTMLRPNMYF |
| 6 | APLQEKVVFG |
| 7 | IALLIMGS |
| 8 | MGSFVPW |
| 9 | RFATPKHR |
| 10 | RQTRAGVF |
| 11 | MHFTIAEG |
| 12 | FLGLGLSGVVPT |
| 13 | GFVKATTV |
| 14 | ITPIHWVK |
| 15 | ILLPLRIN |
| 16 | DTVELAEL |

[Result 1]

Figure 3:
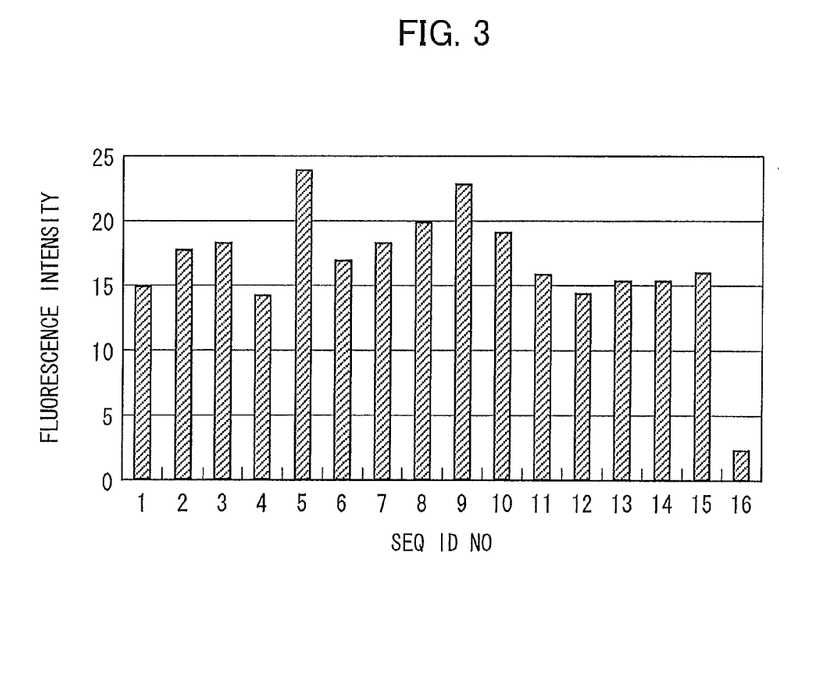
FIG. 3 is a graph showing results of measurement of bonds between peptides and adiponectin.

FIG. 3 shows the measurement results of Example 1 and Comparative Example 1. The peptides having the amino-acid sequences represented by SEQ ID NOs: 1 to 15 (Example 1) were significantly higher in fluorescent intensity than the peptide having the amino-acid sequence represented by SEQ ID NO. 16 (Comparative Example 1). Thus, it was demonstrated that the peptides having the amino-acid sequences represented by SEQ ID NOs: 1 to 15 had bondability with adiponectin.

Example 2

Measurement of Bond Between Peptide and Adiponectin by Enzyme Immunoassay Utilizing Microplate As described below, the bond between adiponectin immobilized onto a microplate and each of peptides tagged with biotin (biotin-tagged peptide) was measured by using enzyme immunoassay.

First, peptides were prepared in such a manner that lysine was added to the C-terminal of each of peptides having amino-acid sequences represented by SEQ ID NOs: 14 and 15. Then, the amino group of a lysine side chain of each of the peptides thus prepared was tagged with biotin so that biotin-tagged peptides were prepared.

5 μg/mL adiponectin (R&D Systems) prepared with PBS was dispensed to wells of a 96-well microplate in an amount of 100 μL per well. Then, the peptides were incubated for 1 hour at 37° C. Adiponectin was thus immobilized in the wells. In order to inhibit nonspecific binding, a blocking solution (Protein-Free Blocking Buffer, PIERCE) was then added to the wells in an amount of 300 μL per well. Then, the peptides were incubated for 2 hours at room temperature. Then, the wells were washed three times with PBST (PBS containing 0.1% (v/v) Tween 20). Then, 1 mM biotin-tagged peptide was added to the wells in an amount of 100 μL per well. Then, the peptides were incubated for 1 hour at room temperature. Then, the wells were washed with PBST again.

Then, HRP-tagged streptavidin (R&D Systems) diluted with 200 parts of the blocking solution (Protein-Free Blocking Buffer, PIERCE) was added to the well in an amount of 100 μL per well. Then, the streptavidin was incubated for 1 hour at room temperature. Then, the wells were washed with PBST. Then, TMB (tetramethylbenzidine) was added to the wells in an amount of 100 μL per well so that they react with each other for 20 minutes. Then, the reaction was stopped by adding 1 M of HCL to the wells in an amount of 100 μL per well. Then, an absorbance at 450 nm was measured by use of a microplate reader (Bio-Rad).

Comparative Example 2

The bond between a peptide having the amino-acid sequence represented by SEQ ID NO. 17 and adiponectin as in Example 2.

Table 3 shows, in abbreviation, amino-acid sequences of the peptides in Example 2 and Comparative Example 2.

TABLE 3

| SEQ ID NO | AMINO-ACID SEQUENCE |
|---|---|
| 14 | ITPIHWVK |
| 15 | ILLPLRIN |
| 17 | SDYYIALG |

[Result 2]

Figure 4:
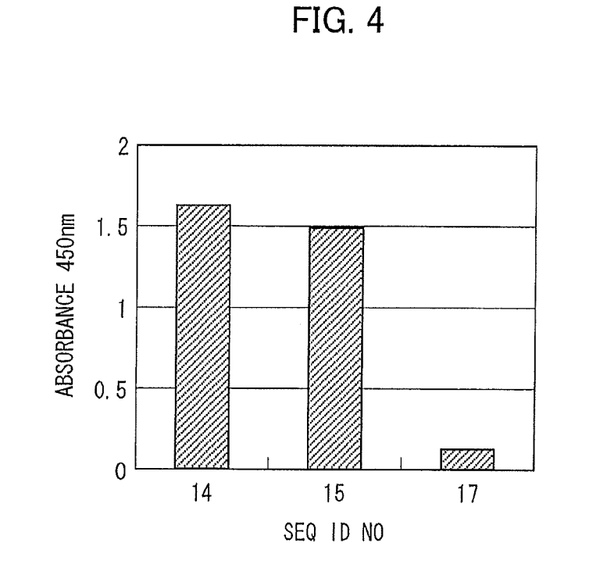
FIG. 4 is a graph showing results of measurement of bonds between peptides and adiponectin.

FIG. 4 shows measurement results of the Example 2 and Comparative Example 2. The peptides having the amino-acid sequences represented by SEQ ID NOs: 14 and 15 (Example 2) were significantly higher in absorbance than the peptide having the amino-acid sequence represented by SEQ ID NO. 17 (Comparative Example 2). Thus, it was demonstrated that the peptides having the amino-acid sequences represented by SEQ ID NOs: 14 and 15 had the bindability with adiponectin.

Example 3

Measurement of Bond Between Peptide with Substitution of Amino Acid and Adiponectin As described below, the bond between each of peptides with conservative substitution of an amino acid and adiponectin was measured on the basis of the group classification of amino acids shown in "(1) Peptide of the present invention."

First, the following peptides were synthesized as in Example 1: peptides having amino-acid sequences represented by SEQ ID NOs: 8 and 9; a peptide obtained by substituting tryptophan of the C-terminal of the amino-acid sequence represented by SEQ ID NO. 8 with tyrosine having the same aromatic ring (i.e., peptide having the amino-acid sequence represented by SEQ ID NO. 18); and a peptide obtained by substituting arginine of the N-terminal of the amino-acid sequence represented by SEQ ID NO. 9 with lysine which is also a basic amino acid (i.e., peptide having the amino-acid sequence represented by SEQ ID NO. 19).

Then, the bond between each of the synthesized peptides and adiponectin was measured as in Example 1.

Table 4 shows, in abbreviation, the amino-acid sequences of the peptides in Example 3.

TABLE 4

| SEQ ID NO | AMINO-ACID SEQUENCE |
|---|---|
| 8 | MGSFVPW |
| 9 | RFATPKHR |

TABLE 4-continued

| SEQ ID NO | AMINO-ACID SEQUENCE |
|---|---|
| 18 | MGSFVPY |
| 19 | KFATPKHR |

[Result 3]

Figure 5:
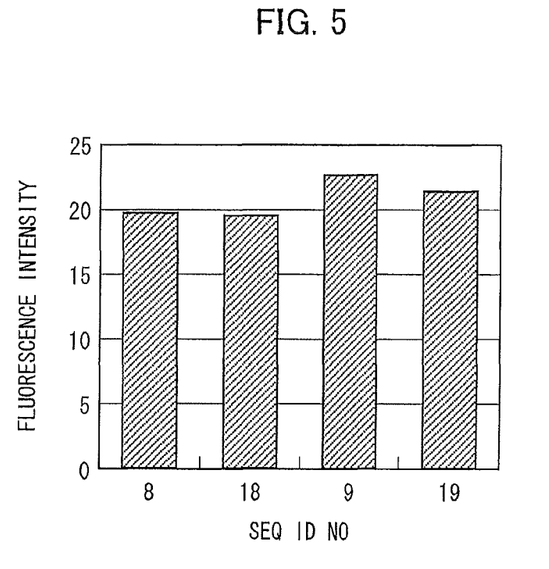
FIG. 5 is a graph showing results of measurement of bonds between peptides and adiponectin.

FIG. 5 shows measurement results of the Example 3. Fluorescent intensities of the peptides having the amino-acid sequences represented by SEQ ID NOs: 18 and 19 were close to those of the peptides having the amino-acid sequences represented by SEQ ID NOs: 8 and 9. Thus, it was demonstrated that the peptides having the amino-acid sequences represented by SEQ ID NOs: 18 and 19 had the bindability with adiponectin.

Industrial Applicability

The peptide of the present invention can be used as an adiponectin-recognition material and as an analytical reagent for analyzing adiponectin. Thus, the present invention is applicable in a field where a biological sample is analyzed.

Reference Signs List

1 Analysis device
2 Supplying section
3 Microchannel
4 Discharging section
5 Immobilizing section
6 Basal plate
7 Analysis measure
8 Analysis section 8
9 Lid
12 Inlet hole
14 Outlet hole

The invention claimed is:

1. A peptide produced by chemical synthesis or recombinant expression having the ability to bind with adiponectin, wherein:
   (i) the peptide is a peptide consisting of the amino-acid sequence of any one of SEQ ID NOs: 1 to 15, 18 or 19; or
   (ii) the peptide is a peptide consisting of an amino-acid sequence in which one amino acid is substituted in the amino-acid sequence of any one of SEQ ID NOs: 1 to 15, and having the bindability with adiponectin; and
   the substitution of the amino acid in the peptide (ii) is conservative substitution between two amino acids selected from any one of the groups:
   (a) asparagine, glutamine, serine, threonine, and glycine;
   (b) asparaginic acid and glutamic acid;
   (c) histidine, lysine, and arginine;
   (d) alanine, isoleucine, leucine, proline, valine, and methionine; and
   (e) phenylalanine, tryptophan, and tyrosine.

2. A substrate onto which a peptide recited in claim 1 is immobilized.

3. A device for analyzing adiponectin, comprising:
   a sample receiving section for receiving a sample; and
   a capturing section for capturing adiponectin, the capturing section being provided inside the sample receiving section, a peptide recited in claim 1 being immobilized onto the capturing section.

4. A device for analyzing adiponectin, comprising:
   a sample receiving section for receiving a sample; and
   a capturing section for capturing adiponectin, the capturing section being provided inside the sample receiving section, a substrate recited in claim 2 being provided in the capturing section.

5. The device as set forth in claim 3 or 4, wherein the sample receiving section has a flow channel.

6. The device as set forth in claim 3 or 4, further comprising analysis means for analyzing said adiponectin captured by the capturing section, the analysis means being directed at an analysis section inside the sample receiving section.

7. The device as set forth in claim 6, wherein the analysis section is provided downstream of the capturing section.

8. The device as set forth in claim 3 or 4, the device being a device in which a microchannel is formed on a basal plate.

9. A tagged peptide having the ability to bind with adiponectin, wherein the peptide consists of the peptide as set forth in claim 1, and a tag that is selected from the group consisting of biotin, avidin, a fluorescent compound, glutathione S-transferase, protein A, alkaline phosphatase, horseradish peroxidase, streptavidin, a sugar chain, a nucleic acid and Green Fluorescent Protein.

10. A method for analyzing adiponectin by using at least one type of peptide recited in claim 1, the method comprising incubating the peptide and a sample, and analyzing the complex of the peptide and adiponectin.

11. A method for analyzing adiponectin by using a substrate recited in claim 2, the method comprising incubating the substrate and a sample, and analyzing a complex of the peptide on the substrate and adiponectin.

12. A method for analyzing adiponectin by using at least one type of tagged peptide recited in claim 9, the method comprising incubating the tagged peptide and a sample, and analyzing the complex of the tagged peptide and adiponectin.

13. A method for analyzing adiponectin by using a substrate on which the tagged peptide recited in claim 9 is immobilized, the method comprising incubating the substrate and a sample, and analyzing a complex of the peptide on the substrate and adiponectin.

\* \* \* \* \*

SEQUENCE LISTING

```
<160> NUMBER OF SEQ ID NOS: 19

<210> SEQ ID NO 1
<211> LENGTH: 8
<212> TYPE: PRT
<213> ORGANISM: Artificial Sequence
<220> FEATURE:
<223> OTHER INFORMATION: Adiponectin binding peptide

<400> SEQUENCE: 1

Val Arg Val Leu Thr Leu Pro Leu
1               5

<210> SEQ ID NO 2
<211> LENGTH: 12
<212> TYPE: PRT
<213> ORGANISM: Artificial Sequence
<220> FEATURE:
<223> OTHER INFORMATION: Adiponectin binding peptide

<400> SEQUENCE: 2

Leu Thr Leu Pro Leu Gln Ala His His Ala Met Glu
1               5                   10

<210> SEQ ID NO 3
<211> LENGTH: 10
<212> TYPE: PRT
```

```
<213> ORGANISM: Artificial Sequence
<220> FEATURE:
<223> OTHER INFORMATION: Adiponectin binding peptide

<400> SEQUENCE: 3

Leu Leu His Gly His Arg Pro Pro Met Pro
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Adiponectin binding peptide

<400> SEQUENCE: 4

Phe Arg Ile His Thr Glu Thr Gly
1               5

<210> SEQ ID NO 5
<211> LENGTH: 11
<212> TYPE: PRT
<213> ORGANISM: Artificial Sequence
<220> FEATURE:
<223> OTHER INFORMATION: Adiponectin binding peptide

<400> SEQUENCE: 5

Ile Leu Thr Met Leu Arg Pro Asn Met Tyr Phe
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Adiponectin binding peptide

<400> SEQUENCE: 6

Ala Pro Leu Gln Glu Lys Val Val Phe Gly
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Adiponectin binding peptide

<400> SEQUENCE: 7

Ile Ala Leu Leu Ile Met Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Adiponectin binding peptide

<400> SEQUENCE: 8

Met Gly Ser Phe Val Pro Trp
1               5

<210> SEQ ID NO 9
<211> LENGTH: 8
<212> TYPE: PRT
<213> ORGANISM: Artificial Sequence
<220> FEATURE:
```

```
<223> OTHER INFORMATION: Adiponectin binding peptide

<400> SEQUENCE: 9

Arg Phe Ala Thr Pro Lys His Arg
1               5

<210> SEQ ID NO 10
<211> LENGTH: 8
<212> TYPE: PRT
<213> ORGANISM: Artificial Sequence
<220> FEATURE:
<223> OTHER INFORMATION: adiponectin binding peptide

<400> SEQUENCE: 10

Arg Gln Thr Arg Ala Gly Val Phe
1               5

<210> SEQ ID NO 11
<211> LENGTH: 8
<212> TYPE: PRT
<213> ORGANISM: Artificial Sequence
<220> FEATURE:
<223> OTHER INFORMATION: adiponectin binding peptide

<400> SEQUENCE: 11

Met His Phe Thr Ile Ala Glu Gly
1               5

<210> SEQ ID NO 12
<211> LENGTH: 12
<212> TYPE: PRT
<213> ORGANISM: Artificial Sequence
<220> FEATURE:
<223> OTHER INFORMATION: Adiponectin binding peptide

<400> SEQUENCE: 12

Phe Leu Gly Leu Gly Leu Ser Gly Val Val Pro Thr
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Adiponectin binding peptide

<400> SEQUENCE: 13

Gly Phe Val Lys Ala Thr Thr Val
1               5

<210> SEQ ID NO 14
<211> LENGTH: 8
<212> TYPE: PRT
<213> ORGANISM: Artificial Sequence
<220> FEATURE:
<223> OTHER INFORMATION: Adiponectin binding peptide

<400> SEQUENCE: 14

Ile Thr Pro Ile His Trp Val Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Adiponectin binding peptide
```

```
<400> SEQUENCE: 15

Ile Leu Leu Pro Leu Arg Ile Asn
1               5

<210> SEQ ID NO 16
<211> LENGTH: 8
<212> TYPE: PRT
<213> ORGANISM: Artificial Sequence
<220> FEATURE:
<223> OTHER INFORMATION: Synthesized peptide

<400> SEQUENCE: 16

Asp Thr Val Glu Leu Ala Glu Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Synthesized peptide

<400> SEQUENCE: 17

Ser Asp Tyr Tyr Ile Ala Leu Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Adiponectin binding peptide

<400> SEQUENCE: 18

Met Gly Ser Phe Val Pro Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: Adiponectin binding peptide

<400> SEQUENCE: 19

Lys Phe Ala Thr Pro Lys His Arg
1               5
```